United States Patent [19]

Enomoto et al.

[11] Patent Number: 5,354,730
[45] Date of Patent: Oct. 11, 1994

[54] URACIL DERIVATIVES AND THEIR HERBICIDAL USE

[75] Inventors: Masayuki Enomoto; Eiki Nagano, both of Hyogo; Ryo Sato; Masaharu Sakai, both of Osaka, all of Japan

[73] Assignee: Sumitomo Chemical Company, Limited, Osaka, Japan

[21] Appl. No.: 66,377

[22] Filed: May 25, 1993

Related U.S. Application Data

[62] Division of Ser. No. 585,917, Sep. 21, 1990, abandoned.

[30] Foreign Application Priority Data

Oct. 2, 1989 [JP] Japan .................. 1-258261
Jul. 6, 1990 [JP] Japan .................. 2-180091

[51] Int. Cl.$^5$ ............... C07D 413/02; C07D 417/02; A01N 43/76; A01N 43/78
[52] U.S. Cl. .................. 504/243; 544/310; 544/312
[58] Field of Search ............. 544/310, 312; 504/243

[56] References Cited

U.S. PATENT DOCUMENTS

| | | | |
|---|---|---|---|
| 3,920,653 | 11/1975 | Wenzelburger et al. | 71/92 |
| 4,640,707 | 3/1987 | Nagano et al. | 71/96 |
| 4,720,297 | 1/1988 | Haga et al. | 71/90 |
| 4,746,352 | 5/1988 | Wenger et al. | 71/90 |
| 4,786,310 | 11/1988 | Haga et al. | 71/90 |
| 4,812,164 | 3/1989 | Wenger et al. | 71/92 |
| 4,820,333 | 4/1989 | Haga et al. | 71/90 |
| 4,824,465 | 4/1989 | Haga et al. | 71/90 |
| 4,859,229 | 8/1989 | Wenger et al. | 71/92 |
| 4,888,045 | 12/1989 | Enomoto et al. | 71/90 |
| 4,981,508 | 1/1991 | Strunk et al. | 71/92 |
| 5,084,084 | 1/1992 | Satow et al. | 71/92 |
| 5,232,898 | 8/1993 | Suchy et al. | 544/105 |

FOREIGN PATENT DOCUMENTS

| | | |
|---|---|---|
| 311135 | 10/1987 | European Pat. Off. |
| 88/10254 | 6/1987 | PCT Int'l Appl. |
| 89/02891 | 9/1987 | PCT Int'l Appl. |
| 90/15057 | 12/1990 | PCT Int'l Appl. |

*Primary Examiner*—Cecilia Tsang
*Assistant Examiner*—Philip I. Datlow
*Attorney, Agent, or Firm*—Birch, Stewart, Kolasch & Birch

[57] ABSTRACT

A compound of the formula:

$$\text{(structure shown)}$$

wherein $R^1$ is a trifluoromethyl group or a pentafluoroethyl group, $R^2$ is a methyl group or an amino group, $R^3$ is a $C_1$-$C_7$ alkyl group, a $C_3$-$C_7$ alkenyl group, a $C_3$-$C_7$ alkynyl group, a halo ($C_1$-$C_6$) alkyl group, a halo ($C_3$-$C_6$) alkenyl group or a $C_1$-$C_4$ alkoxy($C_1$-$C_3$)alkyl group and Y is an oxygen atom or a sulfur atom, which is useful as a herbicide.

11 Claims, No Drawings

URACIL DERIVATIVES AND THEIR HERBICIDAL USE

This application is a divisional of copending application Ser. No. 07/585,917, filed on Sep. 21, 1990, now abandoned, the entire contents of which are hereby incorporated by reference.

The present invention relates to uracil derivatives, and their production and use. More particularly, it relates to uracil derivatives, a process for producing them, and their use as herbicides.

EP-A-311135 discloses some uracil derivatives useful as herbicides. However, these known herbicides are not sufficient in herbicidal potency or have poor selectivity between crop plants and weeds. Their herbicidal activity is thus not necessarily satisfactory.

It has now been found that uracil derivatives of the formula:

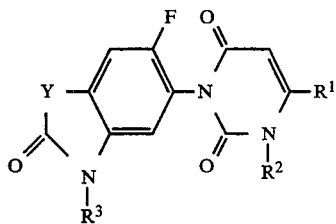

wherein $R^1$ is a trifluoromethyl group or a pentafluoroethyl group, $R^2$ is a methyl group or an amino group, $R^3$ is a $C_1$–$C_7$ alkyl group, a $C_3$–$C_7$ alkenyl group, a $C_3$–$C_7$ alkynyl group, a halo($C_1$–$C_6$)alkyl group, a halo($C_3$–$C_6$)alkenyl group or a $C_1$–$C_4$ alkoxy($C_1$–$C_3$)alkyl group and Y is an oxygen atom or a sulfur atom, show a high herbicidal potency against various weeds with a high selectivity between crop plants and weeds. Thus, they produce a strong herbicidal activity against a wide variety of weeds including broad-leaved weeds, Graminaceous weeds, Commelinaceous weeds and Cyperaceous weeds in agricultural plowed fields by foliar or soil treatment without producing any material phytotoxicity on various agricultural crops such as corn, wheat, barley, rice plant, soybean and cotton. Examples of the broad-leaved weeds include wild buckwheat (*Polygonum convolvulus*), pale smartweed (*Polygonum lapathifolium*), common pursiane (*Portulaca oleracea*), common chickweed (*Stellaria media*), common lambsquarters (*Chenopodium album*), redroot pigweed (*Amaranthus retroflexus*), radish (*Raphanus sativus*), wild mustard (*Sinapis arvensis*), shepherdspurse (*Capsella bursapastoris*), hemp sesbania (*Sesbania exaltata*), sicklepod (*Cassia obtusifolia*), velvetleaf (*Abutilon theophrasti*), prickly sida (*Sida soinosa*), field pansy (*Viola arvensis*), catchweed bedstraw (*Galium aparine*), ivyleaf morningglory (*Ipomoea hederacea*), tall morningglory (*Ipomoea purpurea*), field bindweed (*Convolvulus arvensis*), henbit (*Lamium amplexicaure*), jimsonweed (*Datura stramonium*), black nightshade (*Solanum nigrum*), persian speedwell (*Veronica persica*), common cocklebur (*Xanthium pensylvanicum*), common sunflower (*Helianthus annuus*), scentless chamomile (*Matricaria perforata*), corn marigold (*Chrysanthemum segetum*), purple deadnettle (*Lamium purpureum*), sun spurge (*Euphorbia helioscopia*), spotted spurge (*Euphorbia maculata*), etc.

Examples of Graminaceous weeds include Japanese millet (*Echinochloa frumentacea*), barnyardgrass (*Echinochloa crus-galli*), green foxtail (*Setaria viridis*), large crabgrass (*Digitaria sanguinalis*), annual bluegrass (*Poa annua*), blackgrass (*Alopecurus myosuroides*), oats (*Avena sativa*), wild oats (*Avena fatua*), johnsongrass (*Sorghum halepense*), quackgrass (*Agropyron repens*), bermudagrass (*Cynodon dactylon*), downy brome (*Bromus tectorum*), giant foxtail (*Setaria faberi*), etc. Example of Commelinaceous weeds include asiatic dayflower (*Commelina communis*), etc. Examples of Cyperaceous weeds include rice flatsedge (*Cyperus iria*), purple nutsedge (*Cyperus rotundus*), etc.

The uracil derivatives (I) of the invention are also effective in exterminating paddy field weeds including Graminaceous weeds such as barnyardgrass (*Echinochloa oryzicola*), broad-leaved weeds such as common falsepimpernel (*Lindernia procumbens*), indian toothcup (*Rotala indica*) and waterwort (*Elatine triandra*), Cyperaceous weeds such as water nutgrass (*Cyperus serotinus*), hardstem bulrush (*Scirupus juncoides*), needle spikerush (*Eleocharis acicularis*) and umbrella sedge (*Cyperus difformis*), and others such as monochoria (*Monochoria vaginalis*) and arrowhead (*Sagittaria pygmaea*) without producing any phytotoxicity to rice plants on flooding treatment.

Among the compounds (I), preferred are those wherein $R^1$, $R^2$ and $R^3$ are each as defined above and Y is a sulfur atom. More preferred are those wherein $R^1$ and $R^2$ are each as defined above, $R^3$ is a $C_1$–$C_7$ alkyl group and Y is a sulfur atom.

Typical examples of the preferred compounds are 1-[6-fluoro-3-sec-butyl-2 (3H) -benzothiazolon-5-yl]-3-methyl-4-trifluoromethyl -1,2,3,6-tetrahydropyrimidine-2,6-dione, 1- [6-fluoro-3-isopropyl-2 (3H) -benzothiazolon-5-yl]-3-methyl-4-trifluoromethyl-1,2,3,6-tetrahydropyrimidine-2,6-dione, etc.

The compound (I) is obtainable by the procedures as set forth below.

Procedure (A):

The compound ($R^2$=$CH_3$) is obtainable by reacting a compound of the formula:

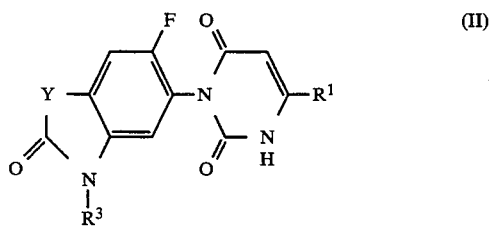

wherein $R^1$ $R^3$ and Y are each as defined above with a methylating agent.

The reaction is usually carried out in the presence of a dehydrohalogenating agent in an inert solvent at a temperature of about 20° to 100° C. for a period of about 0.5 to 8 hours.

In general, the methylating agent and the dehydrohalogenating agent are used respectively in amounts of about to 1.2 equivalents and of about 1 to 3 equivalents to one equivalent of the compound (II). As the methylating agent, there may be used methyl iodide, methyl bromide, methyl chloride, dimethyl sulfate or the like. Examples of the dehydrohalogenating agent are organic bases (e.g. pyridine, triethylamine, N,N-diethylaniline), inorganic bases (e.g. sodium hydroxide, potassium hydroxide, sodium carbonate, potassium carbonate, sodium hydride), alkali metal alkoxides (e.g. sodium methoxide, sodium ethoxide), etc.

Examples of the inert solvent are aliphatic hydrocarbons (e.g. hexane, heptane, ligroin, petroleum ether), aromatic hydrocarbons (e.g. benzene, toluene, xylene), halogenated hydrocarbons (e.g. chloroform, carbon tetrachloride, dichloroethane, chlorobenzene, dichlorobenzene), ethers (e.g. diethyl ether, diisopropyl ether, dioxane, tetrahydrofuran, diethylene glycol dimethyl ether), ketones (e.g. acetone, methyl ethyl ketone, methyl isobutyl ketone, isophorone, cyclohexanone), tertiary amines (e.g. pyridine, triethylamine, N,N-diethylaniline, tributylamine, N-methylmorpholine), acid amides (e.g. formamide, N,N-dimethylformamide, acetamide), sulfur compounds (e.g. dimethylsulfoxide, sulphorane), water, etc. These may be used solely or in combination.

After completion of the reaction, the reaction mixture is subjected to ordinary post-treatment. For instance, the reaction mixture is poured into water, and the precipitated crystal are collected by filtration. Alternatively, the reaction mixture is shaken in combination with water and a water-immiscible organic solvent for extraction, and the extract is concentrated. If desired, any conventional purification procedure such as chromatography, distillation or recrystallization may be applied to the resulting product.

Procedure (B):

The compound ($R^2$=$NH_2$) is obtainable by reacting the compound (II) with an aminating agent.

The reaction is usually carried out in an inert solvent at a temperature of about 20° to 100° C. for a period of about 0.5 to 8 hours.

The aminating agent is normally used in an amount of about 1 to 3 equivalents to one equivalent of the compound (II). As the aminating agent, there may be used 2,4-dinitrophenoxyamine, etc.

Examples of the inert solvent are aliphatic hydrocarbons (e.g. hexane, heptane, ligroin, petroleum ether), aromatic hydrocarbons (e.g. benzene, toluene, xylene), halogenated hydrocarbons (e.g. chloroform, carbon tetrachloride, dichloroethane, chlorobenzene, dichlorobenzene), ethers (e.g. diethyl ether, diisopropyl ether, dioxane, tetrahydrofuran, diethylene glycol dimethyl ether), ketones (e.g. acetone, methyl ethyl ketone, methyl isobutyl ketone, isophorone, cyclohexanone), tertiary amines (e.g. pyridine, triethylamine, N,N-diethylaniline, tributylamine, N-methylmorpholine), acid amides (e.g. formamide, N,N-dimethylformamide, acetamide), sulfur compounds (e.g. dimethylsulfoxide, sulphorane), water, etc.

After completion of the reaction, the reaction mixture is subjected to ordinary post-treatment. For instance, the reaction mixture is poured into water, and the precipitated crystals are collected by filtration. Alternatively, the reaction mixture is shaken in combination with water and a water-immisicible organic solvent for extraction, and the extract is concentrated. If desired, any conventional purification procedure such as chromatography, distillation or recrystallization may be applied to the resulting product.

According to the above procedure (A) or (B), the compounds (I) as shown in Table 1 are obtained.

TABLE 1

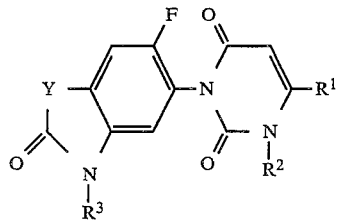

(I)

| $R^1$ | $R^2$ | $R^3$ | Y |
|---|---|---|---|
| $CF_3$ | $CH_3$ | $CH_3$ | S |
| $CF_3$ | $CH_3$ | $C_2H_5$ | S |
| $CF_3$ | $CH_3$ | $(n)C_3H_7$ | S |
| $CF_3$ | $CH_3$ | $(i)C_3H_7$ | S |
| $CF_3$ | $CH_3$ | $(n)C_4H_9$ | S |
| $CF_3$ | $CH_3$ | $(s)C_4H_9$ | S |
| $CF_3$ | $CH_3$ | $(i)C_4H_9$ | S |
| $CF_3$ | $CH_3$ | $(n)C_5H_{11}$ | S |
| $CF_3$ | $CH_3$ | $(n)C_6H_{13}$ | S |
| $CF_3$ | $CH_3$ | $(n)C_7H_{15}$ | S |
| $CF_3$ | $CH_3$ | $CH_2CH{=}CH_2$ | S |
| $CF_3$ | $CH_3$ | $CH(CH_3)CH{=}CH_2$ | S |
| $CF_3$ | $CH_3$ | $CH_2C(H){=}C(CH_3)$ | S |
| $CF_3$ | $CH_3$ | $CH(CH_3)C(H){=}C(CH_3)$ | S |
| $CF_3$ | $CH_3$ | $CH_2C(H){=}C(H)CH_3$ | S |
| $CF_3$ | $CH_3$ | $CH(CH_3)C(H){=}C(H)CH_3$ | S |
| $CF_3$ | $CH_3$ | $CH_2CH{=}C(CH_3)_2$ | S |
| $CF_3$ | $CH_3$ | $CH(CH_3)CH{=}C(CH_3)_2$ | S |
| $CF_3$ | $CH_3$ | $CH{=}C{=}CH_2$ | S |
| $CF_3$ | $CH_3$ | $CH_2C{\equiv}CH$ | S |
| $CF_3$ | $CH_3$ | $CH(CH_3)C{\equiv}CH$ | S |
| $CF_3$ | $CH_3$ | $CH_2C{\equiv}CCH_3$ | S |
| $CF_3$ | $CH_3$ | $CH(CH_3){\equiv}CCH_3$ | S |
| $CF_3$ | $CH_3$ | $CH_2C{\equiv}CC_2H_5$ | S |
| $CF_3$ | $CH_3$ | $CH(CH_3)C{\equiv}CC_2H_5$ | S |
| $CF_3$ | $CH_3$ | $CH_2C{\equiv}CC_3H_7(n)$ | S |
| $CF_3$ | $CH_3$ | $CH(CH_3)C{\equiv}CC_3H_7(n)$ | S |
| $CF_3$ | $CH_3$ | $CH_2OCH_3$ | S |
| $CF_3$ | $CH_3$ | $CH_2OC_2H_5$ | S |
| $CF_3$ | $CH_3$ | $CH_2OC_3H_7(n)$ | S |
| $CF_3$ | $CH_3$ | $CH_2OC_3H_7(i)$ | S |
| $CF_3$ | $CH_3$ | $CH_2OC_4H_9(n)$ | S |
| $CF_3$ | $CH_3$ | $CH_2OC_4H_9(s)$ | S |
| $CF_3$ | $CH_3$ | $CH_2OC_4H_9(i)$ | S |
| $CF_3$ | $CH_3$ | $CH(CH_3)OCH_3$ | S |
| $CF_3$ | $CH_3$ | $CH(CH_3)OC_2H_5$ | S |
| $CF_3$ | $CH_3$ | $CH(CH_3)OC_3H_7(n)$ | S |
| $CF_3$ | $CH_3$ | $CH(CH_3)OC_3H_7(i)$ | S |
| $CF_3$ | $CH_3$ | $CH(CH_3)OC_4H_9(n)$ | S |
| $CF_3$ | $CH_3$ | $CH(CH_3)OC_4H_9(s)$ | S |
| $CF_3$ | $CH_3$ | $CH(CH_3)OC_4H_9(i)$ | S |
| $CF_3$ | $CH_3$ | $C_2H_4OCH_3$ | S |
| $CF_3$ | $CH_3$ | $C_2H_4OC_2H_5$ | S |
| $CF_3$ | $CH_3$ | $CH(CH_3)CH_2OC_2H_5$ | S |
| $CF_3$ | $CH_3$ | $CH_2CH_2F$ | S |
| $CF_3$ | $CH_3$ | $CH_2CF_3$ | S |
| $CF_3$ | $CH_3$ | $CH(CH_3)CH_2F$ | S |
| $CF_3$ | $CH_3$ | $CH(CH_3)CF_3$ | S |
| $CF_3$ | $CH_3$ | $CH_2CCl{=}CH_2$ | S |
| $CF_3$ | $CH_3$ | $CH_2C(H){=}C(H)Cl$ | S |

TABLE 1-continued (I)

Structure: A benzene ring with F at one position, N-C(=O)-CH=C(R¹)-N(R²)-C(=O) forming a ring attached, and Y-C(=O)-N(R³)- substituent.

| R¹ | R² | R³ | Y |
|---|---|---|---|
| CF₃ | CH₃ | CH₂C(H)=CH(Cl) | S |
| C₂F₅ | CH₃ | CH₃ | S |
| C₂F₅ | CH₃ | C₂H₅ | S |
| C₂F₅ | CH₃ | (n)C₃H₇ | S |
| C₂F₅ | CH₃ | (i)C₃H₇ | S |
| C₂F₅ | CH₃ | (n)C₄H₉ | S |
| C₂F₅ | CH₃ | (s)C₄H₉ | S |
| C₂F₅ | CH₃ | (i)C₄H₉ | S |
| C₂F₅ | CH₃ | (n)C₅H₁₁ | S |
| C₂F₅ | CH₃ | (n)C₆H₁₃ | S |
| C₂F₅ | CH₃ | (n)C₇H₁₅ | S |
| C₂F₅ | CH₃ | CH₂CH=CH₂ | S |
| C₂F₅ | CH₃ | CH(CH₃)CH=CH₂ | S |
| C₂F₅ | CH₃ | CH₂C(H)=CH(CH₃) | S |
| C₂F₅ | CH₃ | CH(CH₃)C(H)=CH(CH₃) | S |
| C₂F₅ | CH₃ | CH₂C(H)=C(H)CH₃ | S |
| C₂F₅ | CH₃ | CH(CH₃)C(H)=C(H)CH₃ | S |
| C₂F₅ | CH₃ | CH₂CH=C(CH₃)₂ | S |
| C₂F₅ | CH₃ | CH(CH₃)CH=C(CH₃)₂ | S |
| C₂F₅ | CH₃ | CH=C=CH₂ | S |
| C₂F₅ | CH₃ | CH₂C≡CH | S |
| C₂F₅ | CH₃ | CH(CH₃)C≡CH | S |
| C₂F₅ | CH₃ | CH₂C≡CCH₃ | S |
| C₂F₅ | CH₃ | CH(CH₃)C≡CCH₃ | S |
| C₂F₅ | CH₃ | CH₂C≡CC₂H₅ | S |
| C₂F₅ | CH₃ | CH(CH₃)C≡CC₂H₅ | S |
| C₂F₅ | CH₃ | CH₂C≡CC₃H₇(n) | S |
| C₂F₅ | CH₃ | CH(CH₃)C≡CC₃H₇(n) | S |
| C₂F₅ | CH₃ | CH₂OCH₃ | S |
| C₂F₅ | CH₃ | CH₂OC₂H₅ | S |
| C₂F₅ | CH₃ | CH₂OC₃H₇(n) | S |
| C₂F₅ | CH₃ | CH₂OC₃H₇(i) | S |
| C₂F₅ | CH₃ | CH₂OC₄H₉(n) | S |
| C₂F₅ | CH₃ | CH₂OC₄H₉(s) | S |
| C₂F₅ | CH₃ | CH₂OC₄H₉(i) | S |
| C₂F₅ | CH₃ | CH(CH₃)OC₂H₅ | S |
| C₂F₅ | CH₃ | CH(CH₃)OC₃H₇(n) | S |
| C₂F₅ | CH₃ | CH(CH₃)OC₃H₇(i) | S |
| C₂F₅ | CH₃ | CH(CH₃)OC₄H₉(n) | S |
| C₂F₅ | CH₃ | CH(CH₃)OC₄H₉(s) | S |
| C₂F₅ | CH₃ | CH(CH₃)OC₄H₉(i) | S |
| C₂F₅ | CH₃ | C₂H₄OCH₃ | S |
| C₂F₅ | CH₃ | C₂H₄OC₂H₅ | S |
| C₂F₅ | CH₃ | CH(CH₃)CH₂OC₂H₅ | S |
| C₂F₅ | CH₃ | CH₂CH₂F | S |
| C₂F₅ | CH₃ | CH₂CF₃ | S |
| C₂F₅ | CH₃ | CH(CH₃)CH₂F | S |
| C₂F₅ | CH₃ | CH(CH₃)CF₃ | S |
| C₂F₅ | CH₃ | CH₂CCl=CH₂ | S |

| R¹ | R² | R³ | Y |
|---|---|---|---|
| C₂F₅ | CH₃ | CH₂C(H)=C(H)Cl | S |
| C₂F₅ | CH₃ | CH₂C(H)=CH(Cl) | S |
| CF₃ | NH₂ | CH₃ | S |
| CF₃ | NH₂ | C₂H₅ | S |
| CF₃ | NH₂ | (n)C₃H₇ | S |
| CF₃ | NH₂ | (i)C₃H₇ | S |
| CF₃ | NH₂ | (n)C₄H₉ | S |
| CF₃ | NH₂ | (s)C₄H₉ | S |
| CF₃ | NH₂ | (i)C₄H₉ | S |
| CF₃ | NH₂ | (n)C₅H₁₁ | S |
| CF₃ | NH₂ | (n)C₆H₁₃ | S |
| CF₃ | NH₂ | (n)C₇H₁₅ | S |
| CF₃ | NH₂ | CH₂CH=CH₂ | S |
| CF₃ | NH₂ | CH(CH₃)CH=CH₂ | S |
| CF₃ | NH₂ | CH₂C(H)=CH(CH₃) | S |
| CF₃ | NH₂ | CH(CH₃)C(H)=CH(CH₃) | S |
| CF₃ | NH₂ | CH₂C(H)=C(H)CH₃ | S |
| CF₃ | NH₂ | CH(CH₃)C(H)=C(H)CH₃ | S |
| CF₃ | NH₂ | CH₂CH=C(CH₃)₂ | S |
| CF₃ | NH₂ | CH(CH₃)CH=C(CH₃)₂ | S |
| CF₃ | NH₂ | CH=C=CH₂ | S |
| CF₃ | NH₂ | CH₂C≡CH | S |
| CF₃ | NH₂ | CH(CH₃)C≡CH | S |
| CF₃ | NH₂ | CH₂C≡CCH₃ | S |
| CF₃ | NH₂ | CH(CH₃)C≡CCH₃ | S |
| CF₃ | NH₂ | CH₂C≡CC₂H₅ | S |
| CF₃ | NH₂ | CH(CH₃)C≡CC₂H₅ | S |
| CF₃ | NH₂ | CH₂C≡CC₃H₇(n) | S |
| CF₃ | NH₂ | CH(CH₃)C≡CC₃H₇ | S |
| CF₃ | NH₂ | CH₂OCH₃ | S |
| CF₃ | NH₂ | CH₂OC₂H₅ | S |
| CF₃ | NH₂ | CH₂OC₃H₇(n) | S |
| CF₃ | NH₂ | CH₂OC₃H₇(i) | S |
| CF₃ | NH₂ | CH₂OC₄H₉(n) | S |
| CF₃ | NH₂ | CH₂OC₄H₉(s) | S |
| CF₃ | NH₂ | CH₂OC₄H₉(i) | S |
| CF₃ | NH₂ | CH(CH₃)OCH₃ | S |
| CF₃ | NH₂ | CH(CH₃)OC₂H₅ | S |
| CF₃ | NH₂ | CH(CH₃)OC₃H₇(n) | S |
| CF₃ | NH₂ | CH(CH₃)OC₃H₇(i) | S |
| CF₃ | NH₂ | CH(CH₃)OC₄H₉(n) | S |
| CF₃ | NH₂ | CH(CH₃)OC₄H₉(s) | S |
| CF₃ | NH₂ | CH(CH₃)OC₄H₉(i) | S |
| CF₃ | NH₂ | C₂H₄OCH₃ | S |
| CF₃ | NH₂ | C₂H₄OC₂H₅ | S |
| CF₃ | NH₂ | CH(CH₃)CH₂OC₂H₅ | S |
| CF₃ | NH₂ | CH₂CH₂F | S |
| CF₃ | NH₂ | CH₂CF₃ | S |
| CF₃ | NH₂ | CH(CH₃)CH₂F | S |

TABLE 1-continued structure (I): 4-fluoro-phenyl ring with Y-C(=O)- at position, N-R³ amide, N-ring with R¹, R², and carbonyl groups.

| R¹ | R² | R³ | Y |
|---|---|---|---|
| CF₃ | NH₂ | CH(CH₃)CF₃ | S |
| CF₃ | NH₂ | CH₂CCl=CH₂ | S |
| CF₃ | NH₂ | CH₂C(H)=C(Cl)H | S |
| CF₃ | NH₂ | CH₂C(H)=C(H)Cl | S |
| C₂F₅ | NH₂ | CH₃ | S |
| C₂F₅ | NH₂ | C₂H₅ | S |
| C₂F₅ | NH₂ | (n)C₃H₇ | S |
| C₂F₅ | NH₂ | (i)C₃H₇ | S |
| C₂F₅ | NH₂ | (n)C₄H₉ | S |
| C₂F₅ | NH₂ | (s)C₄H₉ | S |
| C₂F₅ | NH₂ | (i)C₄H₉ | S |
| C₂F₅ | NH₂ | (n)C₅H₁₁ | S |
| C₂F₅ | NH₂ | (n)C₆H₁₃ | S |
| C₂F₅ | NH₂ | (n)C₇H₁₅ | S |
| C₂F₅ | NH₂ | CH₂CH=CH₂ | S |
| C₂F₅ | NH₂ | CH(CH₃)CH=CH₂ | S |
| C₂F₅ | NH₂ | CH₂C(H)=C(H)CH₃ | S |
| C₂F₅ | NH₂ | CH(CH₃)C(H)=C(H)CH₃ | S |
| C₂F₅ | NH₂ | CH₂C(H)=C(H)CH₃ | S |
| C₂F₅ | NH₂ | CH(CH₃)C(H)=C(H)CH₃ | S |
| C₂F₅ | NH₂ | CH₂CH=C(CH₃)₂ | S |
| C₂F₅ | NH₂ | CH(CH₃)CH=C(CH₃)₂ | S |
| C₂F₅ | NH₂ | CH=C=CH₂ | S |
| C₂F₅ | NH₂ | CH₂C≡CH | S |
| C₂F₅ | NH₂ | CH(CH₃)C≡CH | S |
| C₂F₅ | NH₂ | CH₂C≡CCH₃ | S |
| C₂F₅ | NH₂ | CH(CH₃)C≡CCH₃ | S |
| C₂F₅ | NH₂ | CH₂C≡CC₂H₅ | S |
| C₂F₅ | NH₂ | CH(CH₃)C≡CC₂H₅ | S |
| C₂F₅ | NH₂ | CH₂C≡CC₃H₇(n) | S |
| C₂F₅ | NH₂ | CH(CH₃)C≡CC₃H₇(n) | S |
| C₂F₅ | NH₂ | CH₂OCH₃ | S |
| C₂F₅ | NH₂ | CH₂OC₂H₅ | S |
| C₂F₅ | NH₂ | CH₂OC₃H₇(n) | S |
| C₂F₅ | NH₂ | CH₂OC₃H₇(i) | S |
| C₂F₅ | NH₂ | CH₂OC₄H₉(n) | S |
| C₂F₅ | NH₂ | CH₂OC₄H₉(s) | S |
| C₂F₅ | NH₂ | CH₂OC₄H₉(i) | S |
| C₂F₅ | NH₂ | CH(CH₃)OCH₃ | S |
| C₂F₅ | NH₂ | CH(CH₃)OC₂H₅ | S |
| C₂F₅ | NH₂ | CH(CH₃)OC₃H₇(n) | S |
| C₂F₅ | NH₂ | CH(CH₃)OC₃H₇(i) | S |
| C₂F₅ | NH₂ | CH(CH₃)OC₄H₉(n) | S |
| C₂F₅ | NH₂ | CH(CH₃)OC₄H₉(s) | S |
| C₂F₅ | NH₂ | CH(CH₃)OC₄H₉(i) | S |
| C₂F₅ | NH₂ | C₂H₄OCH₃ | S |
| C₂F₅ | NH₂ | C₂H₄OC₂H₅ | S |
| C₂F₅ | NH₂ | CH(CH₃)CH₂OC₂H₅ | S |
| C₂F₅ | NH₂ | CH₂CH₂F | S |
| C₂F₅ | NH₂ | CH₂CF₃ | S |
| C₂F₅ | NH₂ | CH(CH₃)CH₂F | S |
| C₂F₅ | NH₂ | CH(CH₃)CF₃ | S |
| C₂F₅ | NH₂ | CH₂CCl=CH₂ | S |
| C₂F₅ | NH₂ | CH₂C(H)=C(Cl)H | S |
| C₂F₅ | NH₂ | CH₂C(H)=C(H)Cl | S |
| CF₃ | CH₃ | CH₃ | O |
| CF₃ | CH₃ | C₂H₅ | O |
| CF₃ | CH₃ | (n)C₃H₇ | O |
| CF₃ | CH₃ | (i)C₃H₇ | O |
| CF₃ | CH₃ | (n)C₄H₉ | O |
| CF₃ | CH₃ | (s)C₄H₉ | O |
| CF₃ | CH₃ | (i)C₄H₉ | O |
| CF₃ | CH₃ | (n)C₅H₁₁ | O |
| CF₃ | CH₃ | (n)C₆H₁₃ | O |
| CF₃ | CH₃ | (n)C₇H₁₅ | O |
| CF₃ | CH₃ | CH₂CH=CH₂ | O |
| CF₃ | CH₃ | CH(CH₃)CH=CH₂ | O |
| CF₃ | CH₃ | CH₂C(H)=C(H)CH₃ | O |
| CF₃ | CH₃ | CH(CH₃)C(H)=C(H)CH₃ | O |
| CF₃ | CH₃ | CH₂C(H)=C(CH₃)H | O |
| CF₃ | CH₃ | CH(CH₃)C(H)=C(H)CH₃ | O |
| CF₃ | CH₃ | CH₂CH=C(CH₃)₂ | O |
| CF₃ | CH₃ | CH(CH₃)CH=C(CH₃)₂ | O |
| CF₃ | CH₃ | CH=C=CH₂ | O |
| CF₃ | CH₃ | CH₂C≡CH | O |
| CF₃ | CH₃ | CH(CH₃)C≡CH | O |
| CF₃ | CH₃ | CH₂C≡CCH₃ | O |
| CF₃ | CH₃ | CH(CH₃)C≡CCH₃ | O |
| CF₃ | CH₃ | CH₂C≡CC₂H₅ | O |
| CF₃ | CH₃ | CH(CH₃)C≡CC₂H₅ | O |
| CF₃ | CH₃ | CH₂C≡CC₃H₇(n) | O |
| CF₃ | CH₃ | CH(CH₃)C≡CC₃H₇(n) | O |
| CF₃ | CH₃ | CH₂OCH₃ | O |
| CF₃ | CH₃ | CH₂OC₂H₅ | O |
| CF₃ | CH₃ | CH₂OC₃H₇(n) | O |
| CF₃ | CH₃ | CH₂OC₃H₇(i) | O |
| CF₃ | CH₃ | CH₂OC₄H₉(n) | O |
| CF₃ | CH₃ | CH₂OC₄H₉(s) | O |
| CF₃ | CH₃ | CH₂OC₄H₉(i) | O |
| CF₃ | CH₃ | CH(CH₃)OCH₃ | O |
| CF₃ | CH₃ | CH(CH₃)OC₂H₅ | O |
| CF₃ | CH₃ | CH(CH₃)OC₃H₇(n) | O |
| CF₃ | CH₃ | CH(CH₃)OC₃H₇(i) | O |
| CF₃ | CH₃ | CH(CH₃)OC₄H₉(n) | O |
| CF₃ | CH₃ | CH(CH₃)OC₄H₉(s) | O |
| CF₃ | CH₃ | CH(CH₃)OC₄H₉(i) | O |

TABLE 1-continued

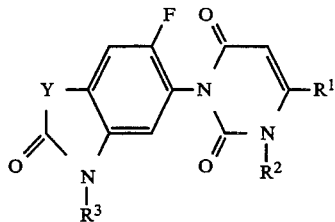

(I)

| R¹ | R² | R³ | Y |
|---|---|---|---|
| CF₃ | CH₃ | C₂H₄OCH₃ | O |
| CF₃ | CH₃ | C₂H₄OC₂H₅ | O |
| CF₃ | CH₃ | CH(CH₃)CH₂OC₂H₅ | O |
| CF₃ | CH₃ | CH₂CH₂F | O |
| CF₃ | CH₃ | CH₂CF₃ | O |
| CF₃ | CH₃ | CH(CH₃)CH₂F | O |
| CF₃ | CH₃ | CH(CH₃)CF₃ | O |
| CF₃ | CH₃ | CH₂CCl=CH₂ | O |
| CF₃ | CH₃ | CH₂C(H)=C(H)Cl | O |
| CF₃ | CH₃ | CH₂C(H)=C(Cl)H | O |
| C₂F₅ | CH₃ | CH₃ | O |
| C₂F₅ | CH₃ | C₂H₅ | O |
| C₂F₅ | CH₃ | (n)C₃H₇ | O |
| C₂F₅ | CH₃ | (i)C₃H₇ | O |
| C₂F₅ | CH₃ | (n)C₄H₉ | O |
| C₂F₅ | CH₃ | (s)C₄H₉ | O |
| C₂F₅ | CH₃ | (i)C₄H₉ | O |
| C₂F₅ | CH₃ | (n)C₅H₁₁ | O |
| C₂F₅ | CH₃ | (n)C₆H₁₃ | O |
| C₂F₅ | CH₃ | (n)C₇H₁₅ | O |
| C₂F₅ | CH₃ | CH₂CH=CH₂ | O |
| C₂F₅ | CH₃ | CH(CH₃)CH=CH₂ | O |
| C₂F₅ | CH₃ | CH₂C(H)=C(H)CH₃ | O |
| C₂F₅ | CH₃ | CH(CH₃)C(H)=C(H)CH₃ | O |
| C₂F₅ | CH₃ | CH₂C(H)=C(H)CH₃ | O |
| C₂F₅ | CH₃ | CH(CH₃)C(H)=C(H)CH₃ | O |
| C₂F₅ | CH₃ | CH₂CH=C(CH₃)₂ | O |
| C₂F₅ | CH₃ | CH(CH₃)CH=C(CH₃)₂ | O |
| C₂F₅ | CH₃ | CH=C=CH₂ | O |
| C₂F₅ | CH₃ | CH₂C≡CH | O |
| C₂F₅ | CH₃ | CH(CH₃)C≡CH | O |
| C₂F₅ | CH₃ | CH₂C≡CCH₃ | O |
| C₂F₅ | CH₃ | CH(CH₃)C≡CCH₃ | O |
| C₂F₅ | CH₃ | CH₂C≡CC₂H₅ | O |
| C₂F₅ | CH₃ | CH(CH₃)C≡CC₂H₅ | O |
| C₂F₅ | CH₃ | CH₂C≡CC₃H₇(n) | O |
| C₂F₅ | CH₃ | CH(CH₃)C≡CC₃H₇(n) | O |
| C₂F₅ | CH₃ | CH₂OCH₃ | O |
| C₂F₅ | CH₃ | CH₂OC₂H₅ | O |
| C₂F₅ | CH₃ | CH₂OC₃H₇(n) | O |
| C₂F₅ | CH₃ | CH₂OC₃H₇(i) | O |
| C₂F₅ | CH₃ | CH₂OC₄H₉(n) | O |
| C₂F₅ | CH₃ | CH₂OC₄H₉(s) | O |
| C₂F₅ | CH₃ | CH₂OC₄H₉(i) | O |
| C₂F₅ | CH₃ | CH(CH₃)OCH₃ | O |
| C₂F₅ | CH₃ | CH(CH₃)OC₂H₅ | O |
| C₂F₅ | CH₃ | CH(CH₃)OC₃H₇(n) | O |
| C₂F₅ | CH₃ | CH(CH₃)OC₃H₇(i) | O |

TABLE 1-continued

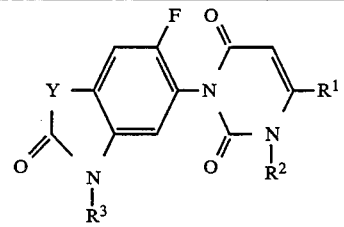

(I)

| R¹ | R² | R³ | Y |
|---|---|---|---|
| C₂F₅ | CH₃ | CH(CH₃)OC₄H₉(n) | O |
| C₂F₅ | CH₃ | CH(CH₃)OC₄H₉(s) | O |
| C₂F₅ | CH₃ | CH(CH₃)OC₄H₉(i) | O |
| C₂F₅ | CH₃ | C₂H₄OCH₃ | O |
| C₂F₅ | CH₃ | C₂H₄OC₂H₅ | O |
| C₂F₅ | CH₃ | CH(CH₃)CH₂OC₂H₅ | O |
| C₂F₅ | CH₃ | CH₂CH₂F | O |
| C₂F₅ | CH₃ | CH₂CF₃ | O |
| C₂F₅ | CH₃ | CH(CH₃)CH₂F | O |
| C₂F₅ | CH₃ | CH(CH₃)CF₃ | O |
| C₂F₅ | CH₃ | CH₂CCl=CH₂ | O |
| C₂F₅ | CH₃ | CH₂C(H)=C(H)Cl | O |
| C₂F₅ | CH₃ | CH₂C(H)=C(Cl)H | O |
| CF₃ | NH₂ | CH₃ | O |
| CF₃ | NH₂ | C₂H₅ | O |
| CF₃ | NH₂ | (n)C₃H₇ | O |
| CF₃ | NH₂ | (i)C₃H₇ | O |
| CF₃ | NH₂ | (n)C₄H₉ | O |
| CF₃ | NH₂ | (s)C₄H₉ | O |
| CF₃ | NH₂ | (i)C₄H₉ | O |
| CF₃ | NH₂ | (n)C₅H₁₁ | O |
| CF₃ | NH₂ | (n)C₆H₁₃ | O |
| CF₃ | NH₂ | (n)C₇H₁₅ | O |
| CF₃ | NH₂ | CH₂CH=CH₂ | O |
| CF₃ | NH₂ | CH(CH₃)CH=CH₂ | O |
| CF₃ | NH₂ | CH₂C(H)=C(H)CH₃ | O |
| CF₃ | NH₂ | CH(CH₃)C(H)=C(H)CH₃ | O |
| CF₃ | NH₂ | CH₂C(H)=C(H)CH₃ | O |
| CF₃ | NH₂ | CH(CH₃)C(H)=C(H)CH₃ | O |
| CF₃ | NH₂ | CH₂CH=C(CH₃)₂ | O |
| CF₃ | NH₂ | CH(CH₃)CH=C(CH₃)₂ | O |
| CF₃ | NH₂ | CH=C=CH₂ | O |
| CF₃ | NH₂ | CH₂C≡CH | O |
| CF₃ | NH₂ | CH(CH₃)C≡CH | O |
| CF₃ | NH₂ | CH₂C≡CCH₃ | O |
| CF₃ | NH₂ | CH(CH₃)C≡CCH₃ | O |
| CF₃ | NH₂ | CH₂C≡CC₂H₅ | O |
| CF₃ | NH₂ | CH(CH₃)C≡CC₂H₅ | O |
| CF₃ | NH₂ | CH₂C≡CC₃H₇(n) | O |
| CF₃ | NH₂ | CH(CH₃)C≡CC₃H₇(n) | O |
| CF₃ | NH₂ | CH₂OCH₃ | O |
| CF₃ | NH₂ | CH₂OC₂H₅ | O |
| CF₃ | NH₂ | CH₂OC₃H₇(n) | O |
| CF₃ | NH₂ | CH₂OC₃H₇(i) | O |
| CF₃ | NH₂ | CH₂OC₄H₉(n) | O |
| CF₃ | NH₂ | CH₂OC₄H₉(s) | O |
| CF₃ | NH₂ | CH₂OC₄H₉(i) | O |
| CF₃ | NH₂ | CH(CH₃)OCH₃ | O |

TABLE 1-continued

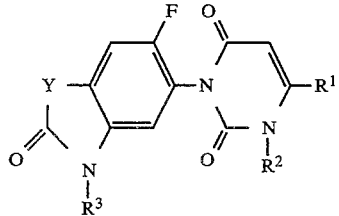

| R¹ | R² | R³ | Y |
|---|---|---|---|
| $CF_3$ | $NH_2$ | $CH(CH_3)OC_2H_5$ | O |
| $CF_3$ | $NH_2$ | $CH(CH_3)OC_3H_7(n)$ | O |
| $CF_3$ | $NH_2$ | $CH(CH_3)OC_3H_7(i)$ | O |
| $CF_3$ | $NH_2$ | $CH(CH_3)OC_4H_9(n)$ | O |
| $CF_3$ | $NH_2$ | $CH(CH_3)OC_4H_9(s)$ | O |
| $CF_3$ | $NH_2$ | $CH(CH_3)OC_4H_9(i)$ | O |
| $CF_3$ | $NH_2$ | $C_2H_4OCH_3$ | O |
| $CF_3$ | $NH_2$ | $C_2H_4OC_2H_5$ | O |
| $CF_3$ | $NH_2$ | $CH(CH_3)CH_2OC_2H_5$ | O |
| $CF_3$ | $NH_2$ | $CH_2CH_2F$ | O |
| $CF_3$ | $NH_2$ | $CH_2CF_3$ | O |
| $CF_3$ | $NH_2$ | $CH(CH_3)CH_2F$ | O |
| $CF_3$ | $NH_2$ | $CH(CH_3)CF_3$ | O |
| $CF_3$ | $NH_2$ | $CH_2CCl=CH_2$ | O |
| $CF_3$ | $NH_2$ | $CH_2CH=CHCl$ | O |
| $CF_3$ | $NH_2$ | $CH_2CH=CHCl$ | O |
| $C_2F_5$ | $NH_2$ | $CH_3$ | O |
| $C_2F_5$ | $NH_2$ | $C_2H_5$ | O |
| $C_2F_5$ | $NH_2$ | $(n)C_3H_7$ | O |
| $C_2F_5$ | $NH_2$ | $(i)C_3H_7$ | O |
| $C_2F_5$ | $NH_2$ | $(n)C_4H_9$ | O |
| $C_2F_5$ | $NH_2$ | $(s)C_4H_9$ | O |
| $C_2F_5$ | $NH_2$ | $(i)C_4H_9$ | O |
| $C_2F_5$ | $NH_2$ | $(n)C_5H_{11}$ | O |
| $C_2F_5$ | $NH_2$ | $(n)C_6H_{13}$ | O |
| $C_2F_5$ | $NH_2$ | $(n)C_7H_{15}$ | O |
| $C_2F_5$ | $NH_2$ | $CH_2CH=CH_2$ | O |
| $C_2F_5$ | $NH_2$ | $CH(CH_3)CH=CH_2$ | O |
| $C_2F_5$ | $NH_2$ | $CH_2CH=CHCH_3$ | O |
| $C_2F_5$ | $NH_2$ | $CH(CH_3)C(CH_3)=CH_2$ | O |
| $C_2F_5$ | $NH_2$ | $CH_2C(CH_3)=CHCH_3$ | O |
| $C_2F_5$ | $NH_2$ | $CH(CH_3)CH=CHCH_3$ | O |
| $C_2F_5$ | $NH_2$ | $CH_2CH=C(CH_3)_2$ | O |
| $C_2F_5$ | $NH_2$ | $CH(CH_3)CH=C(CH_3)_2$ | O |
| $C_2F_5$ | $NH_2$ | $CH=C=CH_2$ | O |
| $C_2F_5$ | $NH_2$ | $CH_2C\equiv CH$ | O |
| $C_2F_5$ | $NH_2$ | $CH(CH_3)C\equiv CH$ | O |
| $C_2F_5$ | $NH_2$ | $CH_2C\equiv CCH_3$ | O |
| $C_2F_5$ | $NH_2$ | $CH(CH_3)C\equiv CCH_3$ | O |
| $C_2F_5$ | $NH_2$ | $CH_2C\equiv CC_2H_5$ | O |
| $C_2F_5$ | $NH_2$ | $CH(CH_3)C\equiv CC_2H_5$ | O |
| $C_2F_5$ | $NH_2$ | $CH_2C\equiv CC_3H_7(n)$ | O |
| $C_2F_5$ | $NH_2$ | $CH(CH_3)C\equiv CC_3H_7(n)$ | O |
| $C_2F_5$ | $NH_2$ | $CH_2OCH_3$ | O |
| $C_2F_5$ | $NH_2$ | $CH_2OC_2H_5$ | O |
| $C_2F_5$ | $NH_2$ | $CH_2OC_3H_7(n)$ | O |
| $C_2F_5$ | $NH_2$ | $CH_2OC_3H_7(i)$ | O |
| $C_2F_5$ | $NH_2$ | $CH_2OC_4H_9(n)$ | O |
| $C_2F_5$ | $NH_2$ | $CH_2OC_4H_9(s)$ | O |
| $C_2F_5$ | $NH_2$ | $CH_2OC_4H_9(i)$ | O |
| $C_2F_5$ | $NH_2$ | $CH(CH_3)OCH_3$ | O |
| $C_2F_5$ | $NH_2$ | $CH(CH_3)OC_2H_5$ | O |
| $C_2F_5$ | $NH_2$ | $CH(CH_3)OC_3H_7(n)$ | O |
| $C_2F_5$ | $NH_2$ | $CH(CH_3)OC_3H_7(i)$ | O |
| $C_2F_5$ | $NH_2$ | $CH(CH_3)OC_4H_9(n)$ | O |
| $C_2F_5$ | $NH_2$ | $CH(CH_3)OC_4H_9(s)$ | O |
| $C_2F_5$ | $NH_2$ | $CH(CH_3)OC_4H_9(i)$ | O |
| $C_2F_5$ | $NH_2$ | $C_2H_4OCH_3$ | O |
| $C_2F_5$ | $NH_2$ | $C_2H_4OC_2H_5$ | O |
| $C_2F_5$ | $NH_2$ | $CH(CH_3)CH_2OC_2H_5$ | O |
| $C_2F_5$ | $NH_2$ | $CH_2CH_2F$ | O |
| $C_2F_5$ | $NH_2$ | $CH_2CF_3$ | O |
| $C_2F_5$ | $NH_2$ | $CH(CH_3)CH_2F$ | O |
| $C_2F_5$ | $NH_2$ | $CH(CH_3)CF_3$ | O |
| $C_2F_5$ | $NH_2$ | $CH_2CCl=CH_2$ | O |
| $C_2F_5$ | $NH_2$ | $CH_2CCl=CHH$ | O |
| $C_2F_5$ | $NH_2$ | $CH_2CH=CHCl$ | O |

Some of the compounds (I) have optical isomers, which are also included within the scope of the invention.

Typical embodiments for production of the compounds (I) are illustratively shown in the following Examples.

Example 1

To a solution of 1-[3-sec-butyl-6-fluoro-2 (3H)benzothiazolon-5-yl]-4-trifluoromethyl-1,2,3,6-tetrahydropyrimidine-2,6-dione (2.0 g) in dimethylformamide (10 g), methyl iodide (0.5 g) and potassium carbonate (1.6 g) were added, and the resultant mixture was heated at 40° to 80° C. for 3 hours. After completion of the reaction, the reaction mixture was poured into water, and the precipitated crystals were collected by filtraction, washed and dried. The residue was purified by column chromatography to give 1-[3-sec-butyl-6-fluoro-2(3H) -benzothiazolon-5-yl]-3-metyl -4-trifluoromethyl-1,2,3,6-tetrahydropyrimidine-2,6-dione (1.0 g ).

H-NMR δ (ppm) [CDCl₃, 60 MHz]: 0.90 (t, J=7 Hz, 3H), 1.48 (d, J=7 Hz, 3H), 1.6–2.3 (m, 2H), 3.45 (s, 3H), 4.0–4.5 (m, 1H), 6.3 (s, 1H), 7.03 (d, J=6 Hz, 1H), 7.32 (d, J=10 Hz, 1H).

Example 2

To a solution of 1-[6-fluoro-3-propargyl-2(3H)benzoxazolon-5-yl]-4-trifluoromethyl-1,2,3,6-tetrahydropyrimidine-2,6-dione (2.0 g) in dimethylformamide (10 g), methyl iodide (0.5 g) and sodium hydride (0.4 g) were added, and the resultant mixture was heated at 40° to 50° C. for 3 hours. After completion of the reaction, the reaction mixture was poured into water, extracted with ethyl acetate, and the organic layer was concentrated under reduced pressure. The residue was purified by column chromatography to give 1-[6-fluoro-3-propargyl-2(3H) -benzoxazolon-5-yl]-3-methyl -4-trifluoromethyl-1,2,3,6-tetrahydropyrimidine-2,6-dione (0.3 g).

Example 3

To a solution of 1-[6-fluoro-3-sec-butyl-2(3H)-benzothiazolon-5-yl]-4-trifluoromethyl-1,2,3,6-tetrahydropyrimidine-2,6-dione (2.0 g) in dimethylformamide (10 g), sodium hydride (0.3 g) and 2,4-dinitrophenoxyamine (1.8 g) were added, and the resultant mixture was heated at 40 to 60° C. for 3 hours. After completion of the reaction, the reaction mixture was poured into water, extracted with ethyl acetate and concentrated. The residue was purified by silica gel column chromatography to give 1-[6-fluoro-3-sec-butyl-2(3H)-benzothiazolon-5-yl]-3-amino-4-trifluoromethyl-1,2,3,6-tetrahydropyrimidine-2,6-dione (0.4 g).

In the same manner as above, the compounds (I) as shown in Table 2 were obtained.

TABLE 2

(I)

| Compound No. | $R^1$ | $R^2$ | $R^3$ | Y | Physical property |
|---|---|---|---|---|---|
| 1 | CF$_3$ | CH$_3$ | CH$_3$ | S | m.p. 102–103° C. |
| 2 | CF$_3$ | CH$_3$ | (s)C$_4$H$_9$ | S | m.p. 84–86° C. |
| 3 | CF$_3$ | CH$_3$ | (i)C$_3$H$_7$ | S | resinous |
| 4 | CF$_3$ | CH$_3$ | (n)C$_3$H$_7$ | S | m.p. 180–181° C. |
| 5 | CF$_3$ | CH$_3$ | CH$_2$CH=CH$_2$ | S | m.p. 61–62° C. |
| 6 | CF$_3$ | CH$_3$ | CH$_2$C≡CH | S | resinous |
| 7 | CF$_3$ | CH$_3$ | CH$_3$<br>\|<br>CHC≡CH | S | resinous |
| 8 | CF$_3$ | CH$_3$ | CH$_3$<br>\|<br>CHCH=CH$_2$ | S | m.p. 146–147° C. |
| 9 | CF$_3$ | CH$_3$ | CH=C=CH$_2$ | S | resinous |
| 10 | CF$_3$ | CH$_3$ | CH$_2$C=CH$_2$<br>\|<br>Cl | S | resinous |
| 11 | CF$_3$ | CH$_3$ | CH$_2$CH$_2$F | S | m.p. 179–180° C. |
| 12 | CF$_3$ | CH$_3$ | CH$_2$OCH$_3$ | S | m.p. 166–167° C. |
| 13 | C$_2$H$_5$ | CH$_3$ | (s)C$_4$H$_9$ | S | m.p. 157–159° C. |
| 14 | CF$_3$ | NH$_2$ | (i)C$_3$H$_7$ | S | resinous |
| 15 | CF$_3$ | NH$_2$ | (s)C$_4$H$_9$ | S | resinous |
| 16 | CF$_3$ | CH$_3$ | CH$_2$C≡CH | O | m.p. 108–111° C. |

The starting compound (II) may be produced according to the following scheme:

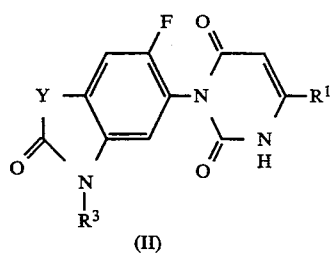

(II)

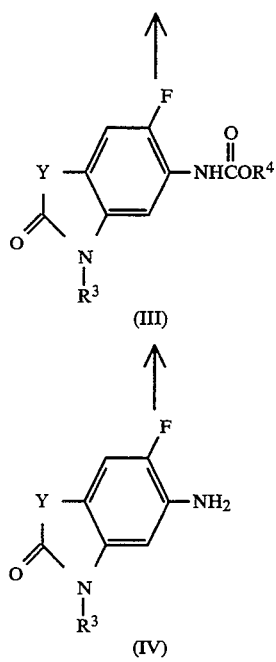

wherein $R^4$ is a $C_1$–$C_6$ alkyl group and $R^1$, $R^3$ and Y are each as defined above.

The reaction at each step in the above scheme will be hereinafter explained in detail.

(1) Preparation of the compound (II) from the compound (III):

The compound (II) may be produced by reacting the compound (III) with a compound of the formula:

$$R^1(NH_2)C=CHCOOR^5 \qquad (V)$$

wherein $R^5$ is a $C_1$–$C_6$ alkyl group and $R^1$ is as defined above usually in the presence of a dehydrogenating agent in an inert solvent at a temperature of about 0° to 200° C. for a period of about 0.5 to 10 hours.

In general, the compound (V) and the dehydrogenating agent are used respectively in amounts of about 1 to 1.2 equivalents and of about 1 to 1.2 equivalents to one equivalent of the compound (III). As the dehydrogenating agent, there may be used an inorganic base (e.g. sodium carbonate, potassium carbonate, sodium hydride), an alkali metal alkoxide (e.g. sodium methoxide, sodium ethoxide), etc.

Examples of the inert solvent are aliphatic hydrocarbons (e.g. hexane, heptane, ligroin, petroleum ether), aromatic hydrocarbons (e.g. benzene, toluene, xylene), ethers (e.g. diethyl ether, diisopropyl ether, dioxane, tetrahydrofuran, diethylene glycol dimethyl ether), tertiary amines (e.g. pyridine, triethylamine, N,N-diethylaniline, tributylamine, N-methylmorpholine), acid amides (e.g. formamide, N,N-dimethylformamide, acetamide), sulfur compounds (e.g. dimethylsulfoxide, sulphorane), etc. These may be used solely or in combination.

After completion of the reaction, the reaction mixture is subjected to ordinary post-treatment. For instance, the reaction mixture is poured into water and extracted with an organic solvent, followed by concentration. If desired, any conventional purification procedure such as chromatography, distillation or recrystallization may be applied to the resulting product.

The compound (II) may be methylated or aminated without isolation to give the compound (I).

A typical embodiment for preparation of the compound (II) is illustratively shown in the following example.

Example 4

To a solution of 3-isopropyl-6-fluoro-5-methoxycarbonylamino -2(3H)-benzothiazolone (2.8 g) in N,N-dimethylformamide (10 g), sodium hydride (0.4 g) and ethyl 3-amino-4,4,4-trifluorocrotonate (0.9 g) were added, and the resultant mixture was heated under reflux for 3 hours. After cooling, the reaction mixture was poured into water and extracted with ethyl acetate. The organic layer was concentrated, and the residue was purified by column chromatography to give 1-[3-isopropyl-6-fluoro-2(3H) -benzothiazolon -5-yl]-4-trifluoromethyl-1,2,3,6-tetrahydropyrimidine -2,6-dione (0.8 g).

H-NMR δ (ppm) [CDCl$_3$, 60 MHz]: 1.55 (6H, d, J=7 Hz), 4.4–5.5 (1H. m). 6.17 (1H, s), 7.0 (1H, d, J=6 Hz), 7.25 (1H, d, J=9 Hz), 9.0–10.1 (1H, m).

In the same manner as above, the compounds (II) as shown in Table 3 were obtained.

TABLE 3

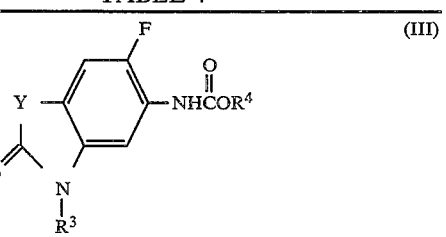
(II)

| R$^1$ | R$^3$ | Y | Physical property |
|---|---|---|---|
| CF$_3$ | CH$_2$C≡CH | O | m.p. 60–64° C. |
| CF$_3$ | (i)C$_3$H$_7$ | S | resinous |

(2) Preparation of the compound (III) from the compound (IV):

The compound (III) may be produced by reacting the compound (IV) with a compound of the formula:

(VI)

wherein R$^5$ is a C$_1$-C$_6$ alkyl group in the existence of a dehydrohalogenating agent in the presence or absence of an inert solvent at a temperature of about 0° to 150° C. for a period of about 0.5 to 10 hours.

Normally, the compound (VI) and the dehydrohalogenating agent are used respectively in amounts of about to 1.5 equivalents and of about 1 to 1.5 equivalents to one equivalent of the compound (IV). As the dehydrohalogenating agent, there may be used an organic base (e.g. pyridine, triethylamine, N,N-diethylaniline), an inorganic base (e.g. sodium hydroxide, potassium hydroxide, sodium carbonate, potassium carbonate, sodium hydride), an alkali metal alkoxide (e.g. sodium methoxide, sodium ethoxide), etc.

Examples of the inert solvent are aromatic hydrocarbons (e.g. benzene, toluene, xylene), halogenated hydrocarbons (e.g. chloroform, carbon tetrachloride), ethers (e.g. diethyl ether, dioxane), etc.

After completion of the reaction, the reaction mixture is subjected to ordinary post-treatment. For instance, the reaction mixture is poured into water and extracted with an organic solvent, followed by concentration. If desired, any conventional purification procedure such as chromatography, distillation or recrystallization may be applied to the resulting product.

A typical embodiment for production of the compound (III) is illustratively shown in the following Example.

Example 5

A mixture of 5-amino-6-fluoro-3-isopropyl-2(3H)-benzothiazolone (2.1 g), N,N-diethyianiline (1.5 g) and methyl chloroformate (1.0 g) was dissolved in 1,2-dichloroethane (10 g), and the resultant mixture was heated under reflux for 3 hours. After cooling, the reaction mixture was washed with water, and the organic layer was concentrated. The residue was washed with methanol to give 6-fluoro-5-methoxycarbonylamino -3-isopropyl-2(3H)-benzothiazolone (2.1 g).

In the same manner as above, the compounds (III) as shown in Table 4 were obtained.

TABLE 4

(III)

| R$^3$ | R$^4$ | Y | Physical property |
|---|---|---|---|
| C$_2$H$_5$ | CH$_3$ | S | m.p. 178–179° C. |
| (i)C$_3$H$_7$ | CH$_3$ | S | m.p. 158–159° C. |
| (s)C$_4$H$_9$ | CH$_3$ | S | m.p. 117–118° C. |
| CH$_2$CH=CH$_2$ | CH$_3$ | S | m.p. 140–141° C. |
| CH$_3$<br>\|<br>CHCH=CH$_2$ | CH$_3$ | S | m.p. 91–92° C. |
| CH$_2$C≡CH | CH$_3$ | S | m.p. 187–188° C. |
| CH$_2$OCH$_3$ | CH$_3$ | S | m.p. 161–162° C. |
| CH$_2$CH$_2$F | CH$_3$ | S | m.p. 199–200° C. |
| CH$_2$C≡CH | CH$_3$ | O | m.p. 161–163° C. |

The compound (IV) can be produced by the method as disclosed in U.S. Pat. No. 4,640,707 or U.S. Pat. No. 4,720,297.

For the practical usage of the compound (I), it is usually formulated with conventional solid or liquid carriers or diluents as well as surface active agents or auxiliary agents into conventional preparation forms such as emulsifiable concentrates, wettable powders, suspensions, water dispersible granules and granules. The content of the compound (I) as the active ingredient in such preparation forms is normally within a range of about 0.02 to 80% by weight, preferably of about 0.05 to 70% by weight. Examples of the solid carrier or diluent are fine powders or granules of kaolin clay, attapulgite clay, bentonite, terra alba, pyrophyllite, talc, diatomaceous earth, calcite, walnut powders, urea, ammonium sulfate and synthetic hydrous silicate, etc. As the liquid carrier or diluent, there may be exemplified aromatic hydrocarbons (e.g. xylene, methylnaphthalene), alcohols (e.g. isopropanol, ethylene glycol, cellosolve), ketones (e.g. acetone, cyclohexanone, isophorone), soybean oil, cotton seed oil, dimethylsulfoxide, N,N-dimethylformamide, acetonitrile, water, etc.

The surface active agent used for emulsification, dispersion or spreading may be of any type, for instance, either anionic or non-ionic. Example of the surface active agent include alkylsulfates, alkylarylsulfonates, dialkylsulfosuccinates, phosphates of polyoxyethylenealkylaryI ethers, polyoxyethylene alkyl ethers, polyoxyethylene alkylaryl ethers, polyoxyethylene polyoxypropylene block copolymer, sorbitan fatty acid esters, polyoxyethylene sorbitan fatty acid esters, etc. Examples of the auxiliary agents include ligninsulfonates, sodium alginate, polyvinyl alcohol, gum arabic, CMC (carboxymethyl celluloses, PAP (isopropyl acid phosphate), etc.

Practical embodiments of the herbicidal composition according to the present invention are illustratively shown in the following examples wherein parts are by weight. The number of the active ingredient corresponds to the one in Table 2.

Formulation Example 1

Fifty parts of any one of Compound Nos. 1, 2, 4. 5, 8, 11 to 13 or 16, 3 parts of calcium ligninsuifonate, 2 parts of sodium laurylsulfate and 45 parts of synthetic hydrous silicate are well mixed while being powdered to obtain a wettable powder.

Formulation Example 2

Five parts of any one of Compound Nos. 1 to 16, 14 parts of polyoxyethylenestyrylphenyl ether, 6 parts of calcium dodecylbenzenesulfonate, 25 parts of xylene and 50 parts of cyclohexanone are well mixed to obtain an emulsifiable concentrate.

Formulation Example 3

Two parts of any one of Compound Nos. 1 to 16, 1 part of synthetic hydrous silicate, 2 parts of calcium ligninsulfonate,. 30 parts of bentonite and 65 parts of kaolin clay are well mixed while being powdered. The mixture is then kneaded with water, granulated and dried to obtain granules.

Formulation Example 4

Twenty-five parts of any one of Compound Nos. 1, 2, 4, 5, 8, 11 to 13 or 16 are mixed with 3 parts of polyoxyethylene sorbitan monooleate, 3 parts of carboxymethyl cellulose and 69 parts of water and pulverized until the particle size of the mixture becomes less than 5 microns to obtain a suspension.

Formulation Example 5

0.05 Part of any one of Compound Nos. 1 to 16, 1 part of synthetic hydrous silicate, 2 parts of calcium ligninsulfonate, 30 parts of bentonite and 66.95 parts of kaolin clay are well mixed while being powdered. The mixture is then kneaded with water, granulated and dried to obtain granules.

The compound (I) thus formulated in any suitable preparation form is useful for pre-emergence or post-emergence control of undesired weeds by soil or foliar treatment as well as flood fallowing treatment. These treatments include application to the soil surface prior to or after planting, incorporation into the soil prior to planting or transplanting, etc. The foliar treatment may be effected by spraying the herbicidal composition containing the compound (I) over the top of plants. It may also be applied directly to the weeds if care is taken to keep the chemical off the crop foliage.

The compound (I) may be used together with any other herbicide to improve its activity as a herbicide, and in some cases, a synergistic effect can be expected. Further, it may be applied in combination with an insecticide, an acaricide, a nematocide, a fungicide, a plant growth regulator, a fertilizer, a soil improver, etc. It is also useful as a herbicide to be employed for orchards, pasture lands, lawns, forests, non-agricultural fields, etc.

The dosage of the compound (I) may vary depending on the prevailing weather conditions, the formulation used, the prevailing season, the mode of application, the soil involved, the crop and weed species, etc. Generally, however, the dosage is from about 0.01 to 80 grams, preferably from about 0.02 to 40 grams, of the active ingredient per are. The herbicidal composition of the invention formulated in the form of an emulsifiable concentrate, a wettable powder, a water-dispersible granule or a suspension may ordinarily be employed by diluting it with water at a volume of about 1 to 10 liters per are, if necessary with addition of an auxiliary agent such as a spreading agent. Examples of the spreading agent include, in addition to the surface active agents as noted above, polyoxyethylene resin acid (ester), ligninsulfonate, abietylenic acid salt, dinaphthylmethanedisulfonate, paraffin, etc. The composition formulated in the form of granules may be normally applied as such without dilution.

The biological data of the compound (I) as herbicides will be illustratively shown in the following Examples wherein the phytotoxicity to crop plants and the herbicidal activity on weeds were observed visually as to the degree of germination as well as the growth inhibition and rated with an index 0, 1, 2, 3, 4, or 5, the numeral "0" indicating no material difference as seen in comparison with the untreated plants and the numeral "5" indicating the complete inhibition or death of the test plants.

The compounds as shown in Table 5 were used for comparison.

TABLE 5

| Compound No. | Structure | Remarks |
| --- | --- | --- |
| A | ![structure] | EP-A-0311135 |
| B | ![structure] | Chloronitrofen |
| C | ![structure] | Benazolin |

Test Example 1

Cylindrical plastic pots (diameter, 10 cm; height, 10 cm) were filled with upland field soil, and the seeds of Japanese millet, oats, tall morningglory and velvetleaf were sowed therein and covered with soil. A designated amount of the test compound formulated in an emulsifiable concentrate as in Formulation Example 2 was diluted with water, and the dilution was sprayed onto the soil surface by means of a small hand sprayer at a spray volume of 10 liters per are. The test plants were grown in a greenhouse for 20 days, and the herbicidal activity was examined. The results are shown in Table 6.

TABLE 6

| Compound No. | Dosage (g/are) | Herbicidal activity | | | |
|---|---|---|---|---|---|
| | | Japanese millet | Oats | Tall morning-glory | Velvet-leaf |
| 1 | 5 | 5 | 5 | 5 | 5 |
| | 1.25 | 5 | 5 | 5 | 5 |
| 2 | 5 | 5 | 5 | 5 | 5 |
| | 1.25 | 5 | 5 | 5 | 5 |
| 3 | 5 | 5 | 5 | 5 | 5 |
| | 1.25 | 5 | 5 | 5 | 5 |
| 4 | 5 | 5 | 5 | 5 | 5 |
| | 1.25 | 5 | 5 | 5 | 5 |
| 5 | 5 | 5 | 5 | 5 | 5 |
| | 1.25 | 5 | 5 | 5 | 5 |
| 6 | 5 | 5 | 5 | 5 | 5 |
| | 1.25 | 5 | 5 | 5 | 5 |
| 7 | 5 | 5 | 5 | 5 | 5 |
| | 1.25 | 5 | 5 | 5 | 5 |
| 8 | 5 | 5 | 5 | 5 | 5 |
| | 1.25 | 5 | 5 | 5 | 5 |
| 8 | 5 | 5 | 5 | 5 | 5 |
| | 1.25 | 5 | 5 | 5 | 5 |
| 9 | 5 | 5 | 5 | 5 | 5 |
| | 1.25 | 5 | 5 | 5 | 5 |
| 10 | 5 | 5 | 5 | 5 | 5 |
| | 1.25 | 5 | 5 | 5 | 5 |
| 11 | 5 | 5 | 5 | 5 | 5 |
| | 1.25 | 5 | 5 | 5 | 5 |
| 12 | 5 | 5 | 5 | 5 | 5 |
| | 1.25 | 5 | 5 | 5 | 5 |
| 13 | 5 | 5 | 5 | 5 | 5 |
| | 1.25 | 5 | 5 | 5 | 5 |
| 14 | 5 | 5 | 5 | 5 | 5 |
| | 1.25 | 5 | 5 | 5 | 5 |
| 15 | 5 | 5 | 5 | 5 | 5 |
| | 1.25 | 5 | 5 | 5 | 5 |
| 16 | 5 | 5 | 5 | 5 | 5 |
| | 1.25 | 5 | 5 | 5 | 5 |
| A | 1.25 | 1 | 0 | 1 | 3 |
| B | 2.5 | 0 | 0 | 0 | 0 |
| | 1.25 | 0 | 0 | 0 | 0 |
| C | 1.25 | 0 | 0 | 0 | 0 |

Test Example 2

Cylindrical plastic pots (diameter, 10 cm; height, 10 cm) were filled with upland field soil, and the seeds of Japanese millet, tall morningglory, radish, velvetleaf and oats were sowed therein and cultivated in a greenhouse for 10 days. A designated amount of the test compound formulated in an emulsifiable concentrate as in Formulation Example 2 was diluted with water containing a spreading agent, and the dilution was sprayed over the foliage of the test plant by means of a small hand sprayer at a spray volume of 10 liters per are. The test plants were further grown in the greenhouse for 20 days, and the herbicidal activity was examined. The results are shown in Table 7.

TABLE 7

| Compound No. | Dosage (g/are) | Herbicidal activity | | | | |
|---|---|---|---|---|---|---|
| | | Japanese millet | Tall morning-glory | Radish | Velvet-leaf | Oats |
| 1 | 10 | 5 | 5 | 5 | 5 | 5 |
| | 1.25 | 5 | 5 | 5 | 5 | 5 |
| 2 | 10 | 5 | 5 | 5 | 5 | 5 |
| | 1.25 | 5 | 5 | 5 | 5 | 5 |
| 3 | 10 | 5 | 5 | 5 | 5 | 5 |
| | 1.25 | 5 | 5 | 5 | 5 | 5 |

TABLE 7-continued

| Compound No. | Dosage (g/are) | Herbicidal activity | | | | |
|---|---|---|---|---|---|---|
| | | Japanese millet | Tall morning-glory | Radish | Velvet-leaf | Oats |
| 4 | 10 | 5 | 5 | 5 | 5 | 5 |
| | 1.25 | 5 | 5 | 5 | 5 | 5 |
| 5 | 10 | 5 | 5 | 5 | 5 | 5 |
| | 1.25 | 5 | 5 | 5 | 5 | 5 |
| 6 | 10 | 5 | 5 | 5 | 5 | 5 |
| | 1.25 | 5 | 5 | 5 | 5 | 5 |
| 7 | 10 | 5 | 5 | 5 | 5 | 5 |
| | 1.25 | 5 | 5 | 5 | 5 | 5 |
| 8 | 10 | 5 | 5 | 5 | 5 | 5 |
| | 1.25 | 5 | 5 | 5 | 5 | 5 |
| 9 | 10 | 5 | 5 | 5 | 5 | 5 |
| | 1.25 | 5 | 5 | 5 | 5 | 5 |
| 10 | 10 | 5 | 5 | 5 | 5 | 5 |
| | 1.25 | 5 | 5 | 5 | 5 | 5 |
| 11 | 10 | 5 | 5 | 5 | 5 | 5 |
| | 1.25 | 5 | 5 | 5 | 5 | 5 |
| 12 | 10 | 5 | 5 | 5 | 5 | 5 |
| | 1.25 | 5 | 5 | 5 | 5 | 5 |
| 13 | 10 | 5 | 5 | 5 | 5 | 5 |
| | 1.25 | 5 | 5 | 5 | 5 | 5 |
| 14 | 10 | 5 | 5 | 5 | 5 | 5 |
| | 1.25 | 5 | 5 | 5 | 5 | 5 |
| 15 | 10 | 5 | 5 | 5 | 5 | 5 |
| | 1.25 | 5 | 5 | 5 | 5 | 5 |
| 16 | 10 | 5 | 5 | 5 | 5 | 5 |
| | 1.25 | 5 | 5 | 5 | 5 | 5 |
| A | 1.25 | 3 | 3 | 5 | 5 | 1 |
| B | 1.25 | 0 | 0 | 0 | 0 | 0 |
| C | 10 | 0 | 2 | 1 | 3 | 0 |
| | 1.25 | 0 | 1 | 0 | 1 | 0 |

Test Example 3

Cylindrical plastic pots (diameter, 8 cm,; height, 12 cm) were filled with paddy field soil, and the seeds of barnyardgrass (Echinochloa oryzicola), broad-leaved weeds (i.e. common falsepimpernel, indian toothcup, waterwort) were sowed in 1 to 2 cm depth. Water was poured therein to make a flooded condition, and rice seedlings of 3-leaf stage were transplanted therein, and the test plants were grown in a greenhouse. Six days (at that time weeds began to germinate) thereafter, a designated amount of the test compound formulated in an emulsifiable concentrate as in Formulation Example 2 and diluted with water (5 ml) was applied to the pots by perfusion. The test plants were grown for an additional 20 days in the greenhouse, and the herbicidal activity and phytotoxicity were examined. The results are shown in Table 8.

TABLE 8

| Compound No. | Dosage (g/are) | Phytotoxicity Rice plant | Herbicidal activity | |
|---|---|---|---|---|
| | | | Barnyard-grass | Broad-leaved weed |
| 2 | 0.16 | 1 | 5 | 5 |
| 3 | 0.16 | 1 | 5 | 5 |
| 4 | 0.16 | 1 | 5 | 5 |
| 5 | 0.16 | 1 | 5 | 5 |
| 6 | 0 16 | 1 | 5 | 5 |
| 7 | 0.16 | 1 | 5 | 5 |
| 8 | 0.16 | 1 | 5 | 5 |
| 9 | 0.16 | 1 | 5 | 5 |
| 10 | 0.16 | 1 | 5 | 5 |
| 11 | 0.16 | 1 | 5 | 5 |
| 12 | 0.16 | 1 | 5 | 5 |
| 13 | 0.16 | 2 | 5 | 5 |
| 16 | 0.16 | 2 | 4 | 5 |
| A | 0.16 | 0 | 2 | 2 |
| B | 0.16 | 0 | 2 | 2 |
| C | 0.16 | 0 | 0 | 0 |

Test Example 4

Vats (33 cm×23 cm×11 cm) were filled with upland field soil, and the seeds of soybean, corn, rice plant, velvetleaf, common cocklebur, tall morningglory, black nightshade, redroot pigweed and green foxtail were sowed therein in 1 to 2 cm depth. A designated amount of the test compound formulated in an emulsifiable concentrate as in Formulation Example 2 was diluted with water, and the dilution was sprayed onto the soil surface by means of a small hand sprayer at a spray volume of 10 liter per are. The test plants were groton in a greenhouse for 20 days, and the herbicidal activity and phytotoxicity were examined. The results are shown in Table 9.

activity and phytotoxicity were examined. The results are shown in Table 10.

TABLE 10

| Compound No. | Dosage (g/a) | Phytotoxicity Wheat | Phytotoxicity Barley | Herbicidal activity Pale smartweed | Herbicidal activity Common chickweed | Herbicidal activity Persian speedwell | Herbicidal activity Field pansy |
| --- | --- | --- | --- | --- | --- | --- | --- |
| 1 | 0.63 | 0 | 1 | 5 | — | 4 | 5 |
| 2 | 0.63 | 0 | 0 | 5 | 5 | 5 | 5 |
|   | 0.32 | 0 | 0 | 5 | 5 | 5 | 5 |
| 3 | 0.63 | 1 | 1 | 5 | 4 | 5 | 5 |
| 4 | 0.63 | — | 1 | 5 | 5 | 5 | 5 |
| 5 | 0.63 | 1 | 1 | 5 | 5 | 5 | 5 |
| 6 | 0.63 | 1 | — | 5 | 5 | 5 | 5 |
|   | 0.32 | 0 | 1 | 5 | 5 | 5 | 5 |
| 7 | 0.63 | — | — | 5 | 5 | 5 | 5 |
|   | 0.32 | 0 | 0 | 5 | 4 | 5 | 5 |
| 8 | 0.63 | 0 | 0 | 5 | 4 | 5 | — |
| 9 | 0.63 | 0 | 0 | 5 | 5 | 5 | — |
| 13 | 0.63 | 0 | 0 | 5 | 4 | 4 | 5 |
| 14 | 0.63 | — | — | 5 | 5 | 5 | 5 |
|   | 0.32 | 1 | 1 | 5 | 5 | 5 | 5 |
| 15 | 0.63 | — | 1 | 5 | 5 | 5 | 5 |
|   | 0.32 | 1 | 1 | 5 | 5 | 5 | 5 |
| C | 0.63 | 0 | 0 | 0 | 0 | 0 | 0 |

TABLE 9

| Compound No. | Dosage (g/a) | Phytotoxicity Soybean | Phytotoxicity Corn | Phytotoxicity Rice plant | Herbicidal activity Velvet leaf | Herbicidal activity Common cocklebur | Herbicidal activity Tall morningglory | Herbicidal activity Black nightshade | Herbicidal activity Redroot pigweed | Herbicidal activity Green foxtail |
| --- | --- | --- | --- | --- | --- | --- | --- | --- | --- | --- |
| 2 | 1.25 | 1 | 0 | 0 | 5 | 5 | 5 | 5 | 5 | 5 |
| 5 | 1.25 | 1 | 0 | 0 | 5 | — | 5 | 5 | 5 | 5 |
| 13 | 1.25 | 1 | 0 | — | 5 | — | 4 | 5 | 5 | 5 |
| 16 | 1.25 | 1 | 0 | 0 | 5 | — | 5 | 5 | 5 | — |
| C | 1.25 | 0 | 0 | 0 | 0 | 0 | 0 | 0 | 0 | 0 |

Test Example 5

Vats (33 cm×23 cm×11 cm) were filled with upland field soil, and the seeds of wheat, barley, pale smartweed, common chickweed, persian speedwell and field pansy were sowed therein in 1 to 2 cm depth. A designated amount of test compound formulated in an emulsifiable concentrate as in Formulation Example 2 was diluted with water, and the dilution was sprayed onto the soil surface by means of a small hand sprayer at a spray volume of 10 liters per are. The test plants were grown in a greenhouse for 27 days, and the herbicidal Test Example 6

Vats (33 cm×23 cm×11 cm) were filled with upland field soil, and the seeds of corn, common cocklebur, velvetleaf, tall morningglory, black nightshade, barnyardgrass and green foxtail were sowed therein and cultivated for 18 days in a greenhouse. A designated amount of the test compound formulated in an emulsifiable concentrate as in Formulation Example 2 was diluted with water, and the dilution was sprayed over the foliage of the test plants by means of a small hand sprayer at a spray volume of 10 liters per are. The test plants were further grown in the greenhouse for 20 days, and the herbicidal activity and phytotoxicity were examined. At the time of the application, the test plants were generally at the 1 to 4 leaf stage and in 2 to 12 cm height, although the growing stage of the test plants varied depending on their species. The results are shown in Table 11.

TABLE 11

| Compound No. | Dosage (g/a) | Phytotoxicity Corn | Herbicidal activity Common cocklebur | Herbicidal activity Velvet-leaf | Herbicidal activity Tall morningglory | Herbicidal activity Black nightshade | Herbicidal activity Barnyardgrass | Herbicidal activity Green foxtail |
| --- | --- | --- | --- | --- | --- | --- | --- | --- |
| 2 | 0.08 | 1 | 5 | 5 | 5 | 5 | 4 | 4 |
| 7 | 0.08 | 1 | 5 | 5 | 5 | 5 | 4 | 4 |
| 6 | 0.08 | 1 | 5 | 5 | 5 | 5 | 5 | 5 |
| C | 0.08 | 0 | 0 | 0 | 0 | 0 | 0 | 0 |

Test Example 7

Vats (33 cm×23 cm×11 cm) were filled with upland field soil, and the seeds of wheat, barley, pale smartweed, catchweed bedstraw, common chickweed, persean speedwell and field pansy were sowed therein and cultivated for 25 days in a greenhouse. A designated amount of the test compound formulated in an emulsifiable concentrate as in Formulation Example 2 was diluted with water, and the dilution was sprayed over the foliage of the test plants by means of a small hand sprayer at a spray volume of 10 liters per are. The test plants were further grown in the greenhouse for 27 days, and the herbicidal activity and phytotoxicity were examined. At the time of the application, the test plants were generally at the 1 to 4 leaf stage and in 2 to 12 cm height, although the growing stage of the test plants varied depending on their species. The results are shown in Table 12.

TABLE 12

| Compound No. | Dosage (g/a) | Phytotoxicity Wheat | Phytotoxicity Barley | Herbicidal activity Pale smartweed | Herbicidal activity Catch weed bedstraw | Herbicidal activity Common chick weed | Herbicidal activity Persian speedwell | Herbicidal activity Field pansy |
|---|---|---|---|---|---|---|---|---|
| 1 | 0.08 | 1 | 1 | 5 | 5 | 5 | 5 | 5 |
| 2 | 0.08 | 1 | 1 | 5 | 5 | 5 | 5 | 5 |
| 3 | 0.08 | 1 | 0 | 5 | — | 4 | 4 | 4 |
| 4 | 0.08 | 0 | 1 | 5 | 5 | 4 | 5 | 5 |
| 5 | 0.08 | 0 | 1 | 5 | 4 | 4 | 5 | 5 |
| 6 | 0.08 | 1 | 1 | 5 | 4 | 5 | 5 | 5 |
| 7 | 0.08 | 1 | 1 | 4 | 4 | 4 | 5 | 5 |
| 8 | 0.08 | 0 | 0 | 5 | — | 4 | 5 | 5 |
| 9 | 0.08 | 1 | 1 | 4 | 4 | — | 5 | 5 |
| 10 | 0.08 | 0 | 0 | 5 | — | 4 | 5 | 5 |
| 14 | 0.08 | 1 | 1 | 5 | — | — | 5 | 5 |
| 15 | 0.08 | 1 | 1 | 5 | — | — | 5 | 5 |
| 16 | 0.08 | 1 | — | 5 | 4 | 5 | 5 | 5 |
| A | 0.08 | 0 | 0 | 0 | 0 | 0 | 1 | 1 |
| B | 0.08 | 0 | 0 | 0 | 0 | 0 | 0 | 0 |
| C | 0.08 | 0 | 0 | 0 | 0 | 0 | 0 | 0 |

Test Example 8

Wagner's pots (1/5000 are) were filled with paddy field soil, and the seeds of broad-leaved weed (e.g. common falsepimpernel, indian toothcup, waterwort) and barnyardgrass were sowed in 1 to 2 cm depth. Water was poured therein to make a flooded condition, and rice seedlings of 2-leaf stage were transplanted therein, and the test plants were grown in a greenhouse. Four days thereafter, a designated amount of the test compound formulated in an emulsifiable concentrate as in Formulation Example 2 and diluted with water (10 ml) was applied to the pots by perfusion. The test plants were grown for an additional 20 days in the greenhouse, and the herbicidal activity and phytotoxicity were examined. The results are shown in Table 13. At the time of the treatment, the depth of water in the pots was kept at 4 cm and following two days, water was let leak a volume corresponding to a 3 cm depth per day.

TABLE 13

| Compound No | Dosage (g/are) | Phytotoxicity Rice plant | Herbicidal activity Broad-leaved weed | Herbicidal activity Barnyardgrass |
|---|---|---|---|---|
| 4 | 0.04 | 1 | 5 | 5 |
| 5 | 0.04 | 1 | 5 | 4 |
| 6 | 0.04 | 1 | 5 | 5 |
| 7 | 0.04 | 0 | 5 | 5 |

Test Example 9

Vats (33 cm×23 cm×11cm) were filled with upland field soil, and the seeds of corn, rice plant, velvetleaf, tall morningglory, black nightshade, redroot pigweed and green foxtail were sowed therein in 1 to 2 cm depth. A designated amount of the test compound formulated in an emulsifiable concentrate as in Formulation Example 2 was diluted with water, and the dilution was sprayed onto the soil surface by means of a small hand sprayer at a spray volume of 10 liters per are. The test plants were grown in a greenhouse for 20 days, and the herbicidal activity and phytotoxicity were examined. The results are shown in Table 14.

TABLE 14

| Compound No. | Dosage (g/a) | Phytotoxicity Corn | Phytotoxicity Rice plant | Herbicidal activity Velvetleaf | Herbicidal activity Tall morningglory | Herbicidal activity Black nightshade | Herbicidal activity Redroot pigweed | Herbicidal activity Green foxtail |
|---|---|---|---|---|---|---|---|---|
| 1 | 1.25 | 0 | 1 | 5 | 5 | 5 | 5 | 4 |
| 2 | 1.25 | 0 | 0 | 5 | 5 | 5 | 5 | 5 |
|   | 0.32 | 0 | 0 | 5 | 4 | 5 | 5 | 4 |
| 3 | 1.25 | 1 | — | 5 | 5 | 5 | 5 | 5 |
|   | 0.32 | 0 | 0 | 5 | 4 | 5 | 5 | 5 |
| 4 | 1.25 | 1 | — | 5 | — | 5 | 5 | 5 |
| 5 | 1.25 | 0 | 0 | 5 | 5 | 5 | 5 | 5 |
| 6 | 1.25 | 0 | 0 | 5 | 5 | 5 | 5 | 5 |
|   | 0.32 | 0 | 0 | 5 | 4 | 5 | 5 | 4 |
| 7 | 1.25 | 1 | 0 | 5 | 5 | 5 | 5 | 5 |
|   | 0.32 | 0 | 0 | 5 | 4 | 5 | 5 | 4 |
| 8 | 1.25 | 0 | 0 | 5 | 4 | 5 | 5 | 5 |
| 10 | 1.25 | 1 | 1 | 5 | 5 | 5 | 5 | 5 |
| 14 | 1.25 | 1 | — | 5 | 4 | 5 | 5 | 5 |
|   | 0.32 | 1 | — | 5 | 4 | 5 | 5 | — |
| 15 | 1.25 | 1 | — | 5 | 5 | 5 | 5 | 5 |
|   | 0.32 | 0 | 1 | 5 | 5 | 5 | 5 | 4 |

TABLE 14-continued

| Compound No. | Dosage (g/a) | Phytotoxicity | | Herbicidal activity | | | | |
| | | Corn | Rice plant | Velvet-leaf | Tall morning-glory | Black night-shade | Redroot pigweed | Green foxtail |
|---|---|---|---|---|---|---|---|---|
| C | 1.25 | 0 | 0 | 0 | 0 | 0 | 0 | 0 |

Test Example 10

Vats (33 cm×23 cm×11 cm) were filled with upland field soil, and the seeds of corn, common cocklebur, velvetleaf, tall morningglory and black nightshade were sowed therein and cultivated for 18 days in a greenhouse. A designated amount of the test compound formulated in an emulsifiable concentrate as in Formulation Example 2 was diluted with water, and the dilution was sprayed over the foliage of the test plants by means of a small hand sprayer at a spray volume of 10 liters per are. The test plants were further grown in the greenhouse for 20 days, and the herbicidal activity and phytotoxicity were examined. At the time of the application, the test plants were generally at the 1 to 4 leaf stage and in 2 to 12 cm height, although the growing stage of the test plants varied depending on their species. The results are shown in Table 15.

TABLE 15

| Compound No. | Dosage (g/a) | Phytotoxicity Corn | Herbicidal activity | | | |
| | | | Common cocklebur | Velvet-leaf | Tall morning-glory | Black night-shade |
|---|---|---|---|---|---|---|
| 1 | 0.08 | 1 | 5 | 5 | 5 | 5 |
| 2 | 0.08 | 1 | 5 | 5 | 5 | 5 |
|   | 0.02 | 1 | 5 | 5 | 4 | 5 |
| 3 | 0.08 | 1 | 5 | 5 | 5 | 5 |
| 4 | 0.08 | 1 | 5 | 5 | 5 | 5 |
| 5 | 0.08 | 1 | 5 | 5 | 5 | 5 |
| 6 | 0.08 | 1 | 5 | 5 | 5 | 5 |
|   | 0.02 | 1 | 4 | 5 | 5 | 5 |
| 7 | 0.08 | 1 | 5 | 5 | 5 | 5 |
|   | 0.02 | 1 | 4 | 5 | 5 | 5 |
| 8 | 0.08 | 1 | — | 5 | 4 | 5 |
| 9 | 0.08 | 1 | 5 | 5 | 5 | 5 |
| 10 | 0.08 | 1 | 5 | 5 | 5 | 5 |
| 13 | 0.08 | 1 | 5 | 5 | 5 | 5 |
| 14 | 0.08 | 1 | 5 | 5 | 5 | 5 |
|   | 0.02 | 0 | 4 | 5 | 4 | 5 |
| 15 | 0.08 | 1 | 5 | 5 | 5 | 5 |
|   | 0.02 | 0 | 4 | 5 | — | 5 |
| C | 0.08 | 0 | 0 | 0 | 0 | 0 |

What is claimed is:

1. (Amended) A compound of the formula:

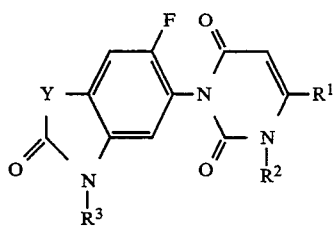

wherein $R^1$ is a trifluoromethyl group or a pentafluoroethyl group, $R^2$ is an amino group, $R^3$ is a $C_1$-$C_7$ alkyl group, a $C_3$-$C_7$ alkenyl group, a $C_3$-$C_7$ alkynyl group, a halo ($C_1$-$C_6$) alkyl group, a halo($C_3$-$C_6$) alkenyl group or a $C_1$-$C_4$ alkoxy($C_1$-$C_3$) alkyl group and Y is an oxygen atom or a sulfur atom.

2. The compound according to claim 1, wherein Y is a sulfur atom.

3. The compound according to claim 1, wherein $R^3$ is a $C_1$-$C_7$ alkyl group.

4. A herbicidal composition which comprises as an active ingredient a herbicidally effective amount of the compound according to claim 1, and an inert carrier or diluent.

5. The compound according to claim 1, wherein $R^1$ is —$OF_3$, $R^2$ is —$NH_2$, $R^3$ is —(i)$C_3H_7$ and Y is sulfur.

6. The compound according to claim 1, wherein $R^1$ is —$OF_3$, $R^2$ is —$NH_2$, $R^3$ is —(s)$C_4H_9$ and Y is sulfur.

7. The compound according to claim 1, wherein Y is an oxygen atom.

8. The compound according to claim 3, wherein Y is a sulfur atom.

9. The compound according to claim 3, wherein Y is an oxygen atom.

10. The compound according to claim 1, wherein Y is a sulfur atom and $R^3$ is a $C_1$-$C_7$ alkyl group or a $C_3$-$C_7$ alkynyl group.

11. The compound according to claim 1, wherein Y is a oxygen atom and $R^3$ is a $C_1$-$C_7$ alkyl group or a $C_3$-$C_7$ alkynyl group.

* * * * *